(12) United States Patent
Mummert et al.

(10) Patent No.: US 11,554,258 B2
(45) Date of Patent: Jan. 17, 2023

(54) SYRINGE WITH SNAP-IN ENTERAL CONNECTION FEATURE

(71) Applicant: Becton, Dickinson and Company, Franklin Lakes, NJ (US)

(72) Inventors: Joseph Mummert, Ramsey, NJ (US); Erik Ferrier, Cranford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 400 days.

(21) Appl. No.: 16/801,814

(22) Filed: Feb. 26, 2020

(65) Prior Publication Data

US 2021/0260356 A1     Aug. 26, 2021

(51) Int. Cl.
*A61M 39/10*     (2006.01)
*A61M 5/31*     (2006.01)

(52) U.S. Cl.
CPC ...... *A61M 39/1011* (2013.01); *A61M 5/3134* (2013.01); *A61M 2039/1038* (2013.01); *A61M 2039/1094* (2013.01); *A61M 2205/276* (2013.01)

(58) Field of Classification Search
CPC ............ A61M 39/1011; A61M 5/3134; A61M 2039/1038; A61M 2039/1094; A61M 2205/276
See application file for complete search history.

(56) References Cited

U.S. PATENT DOCUMENTS

| | | | |
|---|---|---|---|
| 10,661,030 B1* | 5/2020 | Murray | A61M 5/3134 |
| 2014/0012204 A1* | 1/2014 | Bosshardt | A61M 39/1011 604/187 |
| 2014/0171875 A1* | 6/2014 | Poncon | A61M 39/1011 604/192 |

(Continued)

FOREIGN PATENT DOCUMENTS

| | | |
|---|---|---|
| WO | 2018067629 A1 | 4/2018 |
| WO | 2018165616 A2 | 9/2018 |

OTHER PUBLICATIONS

PCT International Search Report and Written Opinion in PCT/US2021/019380 dated Jun. 11, 2021, 11 pages.

(Continued)

*Primary Examiner* — David Bochna
(74) *Attorney, Agent, or Firm* — Servilla Whitney LLC

(57) ABSTRACT

A syringe having barrel defining an outer circumferential surface, and a distal end including a non-luer tip that is not connectable to an intravenous device. The syringe barrel defines a snap-in, syringe engagement feature, adjacent to its distal end, oriented on its outer circumferential surface, which is selectively insertable within a bore of a complementary enteral collar. A proximal end of the enteral collar has a snap-in, enteral collar engagement feature, in the bore of the collar. In some embodiments, the snap-in, enteral collar engagement feature includes one or more cantilever snap joints, which engage a recess in the syringe engagement feature, upon axial insertion of the syringe tip into the (Continued)

bore of the collar. In some embodiments, the enteral collar engagement feature includes a discontinuous-annular snap joint. The enteral collar is sized to permit connection to an enteral device and prevent connection to a device having a luer connector.

18 Claims, 5 Drawing Sheets

(56) References Cited

U.S. PATENT DOCUMENTS

| | | | | |
|---|---|---|---|---|
| 2015/0283372 A1* | 10/2015 | Maritan | ............. | A61M 39/1011 29/446 |
| 2015/0343155 A1* | 12/2015 | Zenker | ............... | A61M 39/1011 604/243 |
| 2016/0158518 A1* | 6/2016 | Hallynck | ........... | A61M 39/1011 604/533 |
| 2016/0250415 A1* | 9/2016 | Yagi | ................... | A61M 39/1011 604/187 |
| 2018/0071507 A1* | 3/2018 | Naftalovitz | ........ | A61M 39/1011 |
| 2018/0099136 A1 | 4/2018 | Di Ubaldi et al. | | |
| 2018/0289941 A1* | 10/2018 | Di Ubaldi | .......... | A61M 39/1011 |
| 2018/0369559 A1* | 12/2018 | Iwakata | ............. | A61M 39/1011 |
| 2019/0336743 A1 | 11/2019 | Wolkenstoerfer | | |
| 2020/0171245 A1* | 6/2020 | Zucchelli | ............ | A61M 5/3134 |
| 2021/0085951 A1* | 3/2021 | Iwakata | ............. | A61M 39/1011 |
| 2021/0131596 A1* | 5/2021 | Mitrovic | ............ | A61M 39/1011 |
| 2021/0236744 A1* | 8/2021 | Murray | ................ | A61M 5/3134 |
| 2021/0283343 A1* | 9/2021 | Mills | ................... | A61M 39/1011 |

OTHER PUBLICATIONS

"Snap-Fit Joints for Plastics—A Design Guide", Bayer MaterialScience (2013), 26 pages.

* cited by examiner

SYRINGE WITH SNAP-IN ENTERAL CONNECTION FEATURE

TECHNICAL FIELD

Aspects of the present disclosure relate to a syringe with an enteral connection feature that prevents connection to non-enteral devices.

BACKGROUND

Enteral nutrition involves delivery of nutrient formula or medicine to the gastrointestinal tract. Administration of nutrients to a patient can be accomplished with an enteral feeding system, assembly or device. Enteral feeding systems typically utilize catheters inserted into a patient's nose or mouth, through which nutrients are administered to the gastrointestinal tract. A syringe or another device may be connected to the catheter to deliver the nutrients through the catheter. Nutrients and food may also be directly administered to a patient's mouth by a syringe, which may be referred to as an "oral syringe" or "oral delivery" of medication and does not require connection to a catheter or other device. Intravenous catheters are inserted into the vasculature of patients to effect intravascular treatment, which delivering medication through the circulatory or cardiovascular system by accessing any blood vessel. Such catheters include intravenous (IV) catheters, which are inserted into veins, and intra-arterial catheters, which are inserted into arteries.

Syringes are used to deliver fluids for a variety of medical applications, including, for example, oral delivery of nutrients, storage and delivery of fluid to enteral systems by connecting the syringe to an enteral connection, and intravenous delivery of fluids or medication. Delivery of medication through intravenous syringes involves connecting the distal end of a syringe to a catheter by a luer connection. A standard male luer tip or standard male connector has specifications as provided by the International Organization for Standardization (ISO) defined in ISO 594-1:1986 and 594-2:1998, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A standard female luer hub or standard female luer connector may have a 6% taper that decreases from the open proximal end to the distal end and an inner cross-sectional diameter at the open proximal end measuring between about 0.168 inches (4.270 mm) to about 0.170 inches (4.315 mm). In devices that have standard female luer connectors that incorporate tabs or lugs for connection to a corresponding male luer lock connector, the outer cross-sectional diameter of the standard female luer connector, including the lugs, is in the range from about 0.307 inches (7.80 mm) to about 0.308 inches (7.83 mm). In devices that have standard female luer connectors that do not incorporate tabs or lugs for connection to a corresponding male luer lock connector, the outer cross-sectional diameter may be about 0.224 inches (5.700 mm) for rigid connectors and about 0.265 inches (6.730 mm) for semi-rigid connectors, based on the maximum outside diameter of the standard female luer connector at the base of the lugs of ISO 594-2. The minimum length of the standard luer tip and/or the standard luer hub is 0.295 inches (7.500 mm), according to ISO 594-1. As used herein, the phrases "standard male luer connector," "standard male luer tip," "standard female luer hub" and "standard female luer connector" shall refer to connectors having the above dimensions.

Delivery of enteral fluid such as breast milk or formula from a syringe having a barrel and a plunger in the barrel is achieved by advancing the plunger into the barrel to pressurize the fluid within the barrel and discharge the fluid from the distal tip of the syringe. Oral dose syringes have a barrel with distal tip defining a channel having a diameter substantially larger than the diameter of a needle cannula. For a typical oral syringe, the distal tip defines a smooth exterior surface that is insertable into the mouth of a patient to orally introduce medication or other fluids into a patient.

Limiting the use of standard luer tips and connectors to use with vascular access systems is one consensus accepted by device manufacturers and regulatory bodies. For example, the recent adoption of ISO 80369-3 provides a uniform standard for small bore connectors for enteral applications. However, the adoption of ISO 830369-3 will result in a variety of syringe types to deliver fluids to patients intravenously, orally and enterally. It would be desirable to provide a syringe that could be used to connect to enteral systems having enteral connections meeting the ISO 80369-3 standard and also be used as on oral syringe, while preventing connection to standard luer tips and connectors.

SUMMARY

A first aspect of the present disclosure pertains to syringe comprising a syringe barrel having a distal end, an open proximal end, and a sidewall extending between the distal end to the open proximal end, the sidewall defining a chamber, an outer circumferential surface, and a snap-in, syringe engagement feature oriented on the outer circumferential surface adjacent the distal end thereof; a non-luer tip oriented on the distal end of the syringe barrel, dimensioned such that the non-luer tip is not connectable to an intravenous device, the non-luer tip defining a fluid pathway in fluid communication with the chamber; an enteral collar, defining a bore in communication with a distal end and a proximal end thereof, the bore having a snap-in, enteral collar engagement feature oriented at the proximal end of the enteral collar that is complementary to and engageable with the syringe engagement feature, the enteral collar engagement feature selectively biased initially in a direction away from a centerline of the bore upon initial axial insertion and advancement of the syringe tip into the bore and then biased in a direction toward the bore centerline upon snap-in engagement with the syringe engagement feature; and the enteral collar surrounding the non-luer tip when the syringe engagement feature is engaged with the enteral collar engagement feature, and the enteral collar being sized to permit connection to an enteral device and prevent connection to a device having a luer connector.

A second aspect of the present disclosure pertains to a syringe comprising a syringe barrel having a distal end, an open proximal end, and a sidewall extending between the distal end to the open proximal end; the sidewall defining a chamber, an outer circumferential surface and a snap-in, syringe engagement feature radially projecting from the outer circumferential surface adjacent the distal end thereof; a non-luer tip oriented on the distal end of the syringe barrel, dimensioned such that the non-luer tip is not connectable to an intravenous device, the non-luer tip defining a fluid pathway in fluid communication with the chamber; an enteral collar, defining a bore in communication with a distal end and a proximal end thereof, threads formed in the bore on the distal end thereof, for engaging a threaded, non-luer connector, the bore having a snap-in, enteral collar engagement feature oriented at the proximal end of the enteral collar that is complementary to and engageable with the syringe engagement feature, the enteral collar engagement feature axially separated from the threads; a concave recess formed on one of the engagement features and a complementary mating convex projection on the other of the engagement features; the enteral collar engagement feature selectively biased initially in a direction away from a centerline of the bore upon initial axial insertion and advancement of the syringe tip into the bore and then biased in a direction toward the bore centerline upon snap-in engagement with the syringe engagement feature; and the enteral collar surrounding the non-luer tip when the syringe engagement feature is engaged with the enteral collar engagement feature, and the enteral collar being sized to permit connection to an enteral device and prevent connection to a device having a luer connector.

Another aspect of the present disclosure pertains to a syringe comprising a barrel having a distal end, an open proximal end, and a sidewall extending between the distal end to the open proximal end; the sidewall defining a chamber, an outer circumferential surface, and a plurality of snap-in, syringe engagement features oriented about and radially projecting from the outer circumferential surface adjacent the distal end thereof, each syringe engagement feature defining a recess; a non-luer tip oriented on the distal end of the syringe barrel, dimensioned such that the non-luer tip is not connectable to an intravenous device, the non-luer tip defining a fluid pathway in fluid communication with the chamber; an enteral collar, defining a bore in communication with a distal end and a proximal end thereof, threads formed in the bore on the distal end thereof, for engaging a threaded, non-luer connector, the bore having a snap-in, enteral collar engagement feature, for engagement with a corresponding syringe engagement feature, the enteral collar engagement feature axially separated from the threads and oriented at the proximal end of the enteral collar; the enteral collar engagement feature formed as a discontinuous-annular snap joint, including a plurality of cantilever snap joints, each cantilever snap joint including a cantilever arm, a proximal end of the arm coupled to the bore of the enteral collar and a hook coupled to a distal end of the arm, the hook projecting toward a centerline of the bore, for snap-in engagement with the recess of its corresponding syringe engagement feature; and the enteral collar surrounding the non-luer tip when the syringe engagement feature is engaged with the enteral collar engagement feature, and the enteral collar being sized to permit connection to an enteral device and prevent connection to a device having a luer connector.

BRIEF DESCRIPTION OF THE DRAWINGS

To facilitate understanding, identical reference numerals have been used, where possible, to designate identical elements that are common to the figures. The figures are not drawn to scale.

DETAILED DESCRIPTION

Figure 1:
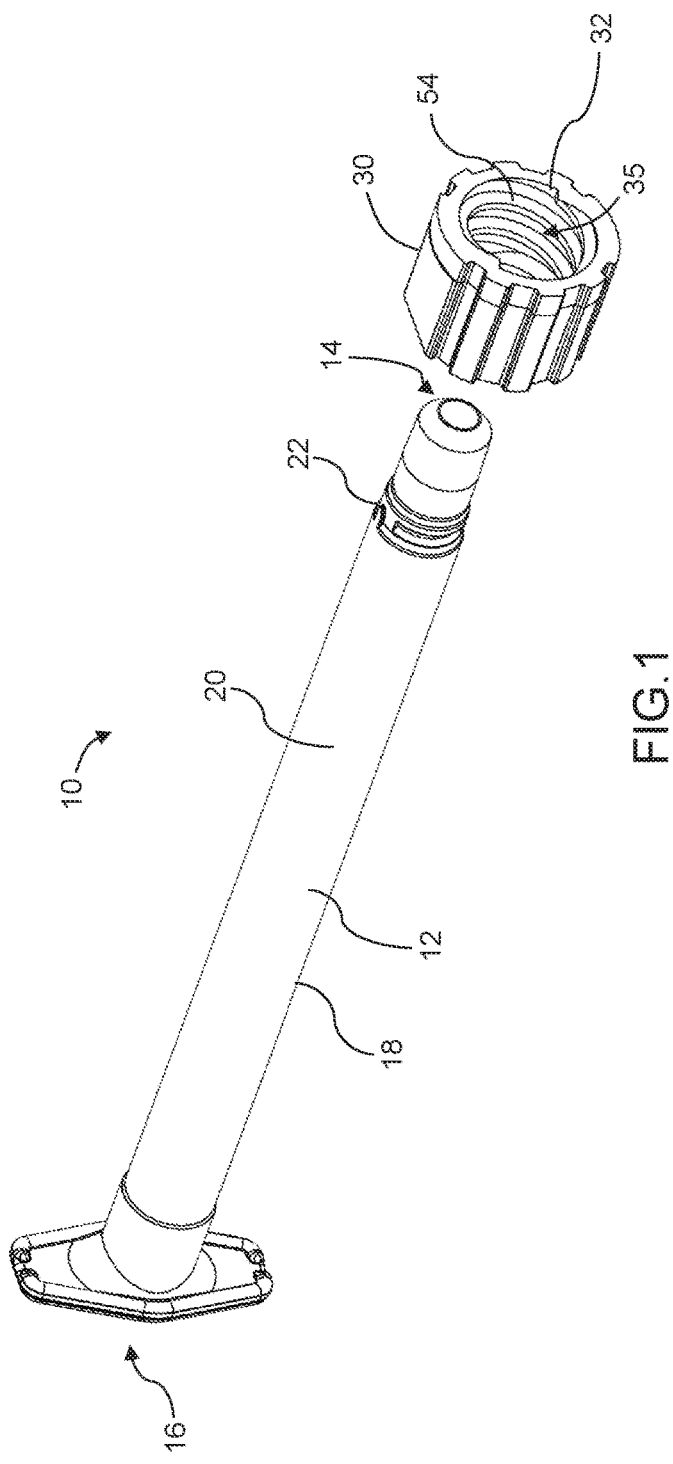
FIG. 1 is a perspective view of a concentrically aligned syringe and collar according to one embodiment.
Figure 2:
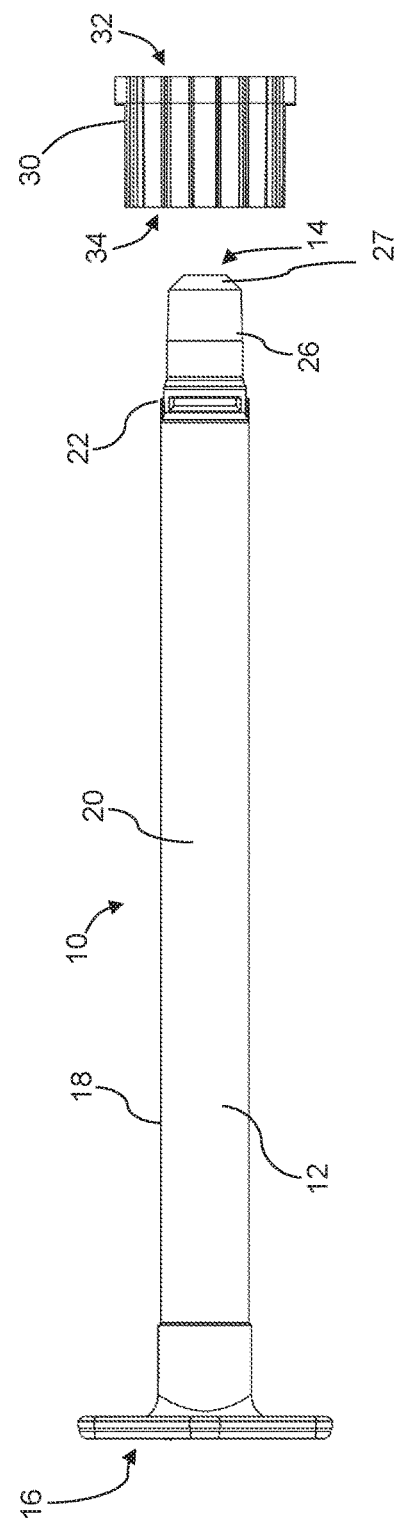
FIG. 2 is a side view of the syringe and collar shown in FIG. 1.

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and the proximal end of the device is the end away from the patient and closest to a practitioner.

The term "not connectable" with respect to male and female connectors refers to a connector having a shape, size, dimension or structure that prevents mating connection to another connector. For example, a female luer connector has a shape, size, dimension and/or structure that prevents it from forming a mating connection with a male non-luer connector and is thus not connectable with respect to the male non-luer connector. Such a female luer connector, however, has a shape, size, dimension and/or structure that permits formation of a mating connection with a male luer connector and is, thus, connectable with respect to the male luer connector. In another example, a female non-luer connector has a shape, size, dimension and/or structure that prevents formation of a mating connection with a male luer connector and is, thus, not connectable with respect to the male luer connector. Such a female non-luer connector has a shape, size dimension and/or structure that permits formation of a mating connection with a male non-luer connector and is thus connectable connector with respect to the male non-luer connector.

As used herein, the term "dimension" shall include the length, diameter or width of a geometric shape or the geometrically shaped components described herein. The term "cross-sectional diameter" shall include the measurement of the longest distance or greatest distance between two points on an edge of a cross-section of an object or component with a circular or non-circular cross-section.

The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

One or more embodiments provide a syringe that has an enteral collar that will enable the syringe meet ISO 80369-3 misconnection requirements. In one or more embodiments, the syringe is a non-luer tapered oral syringe with features on the barrel to accept a collar that prevents connection to intravenous devices. In one or more embodiments, the features include snap/lock features which will allow an enteral collar to be placed and locked onto the syringe. In one or more embodiments, after the enteral collar is attached to the syringe, the collar will not translate or rotate relative to the syringe, however, in other embodiments, the collar selectively translates and/or rotates relative to the syringe. According to one or more embodiments, the syringe can be utilized to draw-up, fill and administer oral medication and fluids as normal oral syringes are currently used, and after the enteral collar is attached the syringe, it will be compliant to ISO 80369-3 and able to be utilized for enteral administration. The syringe according to one or more embodiments does not require any workflow changes in the pharmacy or at patient bed side to deliver oral medication. Thus, one or more embodiments provide a syringe that can be used for two functions, namely oral administration and enteral administration.

One or more embodiments provide a syringe that can be connected to enteral feeding sets and feeding tubes. In the industry, the connection is referred to as ENFit and is compliant to ISO 80369-3. According to one or more embodiments, a syringe is provided that permits the syringe to be connected to enteral tubing and enteral devices such as feeding bags and prevents connection to non-enteral devices, such as intravenous lines, urinary catheters and ventilator tubing. One or more embodiments provide a syringe that is compliant with ENFit devices and ISO 80369-3 and the syringe is not be compatible with a luer connection, thus preventing misadministration of an enteral feeding or medication by the wrong route. Thus, a syringe is provided that when a collar is attached, it has a connector has a unique enteral-specific design that provides a simple way to reduce the risk of enteral tube feeding misconnections and improve patient safety. Furthermore, after the collar is connected, the collar does not allow connectivity with any other connector for any other clinical use such as intravenous devices. According to one or more embodiments, a syringe is provided that when a collar is attached, provides an enteral-specific syringe that can be used to administer medicine, flush, hydrate, or bolus feed through the new ENFit feeding tubes and extension sets compliant with ISO 80369-3. One or more embodiments provide a syringe having a collar that does not connect with standard luer connectors that are compliant with ISO Standard 594/1 and 594/2. Thus, an embodiment of the disclosure provides a syringe having a connector with a dimension that is not compatible with standard sized intravenous connectors and ports to keep the two from being inadvertently coupled mechanically.

Aspects of the present disclosure pertain a syringe having an enteral collar with a male connector that prevents misconnection to other non-compatible female connectors. A male connector shall be defined herein as a male connector that has a shape, size, dimension or structure that differs from a non-compatible female connector. Non-compatible female connectors may include standard female luer connectors, which conform to ISO 594-1:1986 and 594-2:1998.

In one or more embodiments, non-compatible collars having female connectors may have a shape, size, dimension or structure that does not conform to ISO 594-1:1986 or ISO 594-2:1998. In such embodiments, the non-compatible female connector may have a shape, size, dimension or structure that prevents it from being characterized or defined as a female luer connector as defined above or according ISO 594-1:1986 or ISO 594-2:1998. In one or more specific embodiments, non-compatible female connectors may have length and/or cross-sectional diameter that differs from a female luer connector as defined above or according ISO 594-1:1986 or ISO 594-2:1998. In a more specific embodiment, the non-compatible female connector may have a taper that differs from a luer connector as defined above or according ISO 594-1:1986 or ISO 594-2:1998. In an even more specific embodiment, the non-compatible female connector may have a more gentle taper (for example, 5% taper) than a female luer connector as defined above or according ISO 594-1:1986 or ISO 594-2:1998, a cross-sectional diameter that is smaller than a female luer connector as defined above or according ISO 594-1:1986 or ISO 594-2:1998 and/or a longer length than a female luer connector as defined above or according ISO 594-1:1986 or ISO 594-2:1998.

Referring to FIGS. 1-3 and 7, a syringe 10 comprises a syringe barrel 12 having a distal end 14, an open proximal end 16, and a sidewall 18 extending between the distal end 14 to the open proximal end 16. The sidewall 18 defines an interior chamber 20, and a snap-in, syringe engagement feature 22 adjacent the distal end 14 of the syringe barrel 12. The syringe engagement feature 22 includes a pair of opposed, concave recesses 23, which as shown in this embodiment respectively comprise a trapezoidal cross-sectional profile, including an undercut surface 24. In other embodiments, the concave recesses 23 have other cross-sectional profiles, for example square or semicircular or triangular profiles. In some embodiments, the syringe engagement feature 22 has one concave recess or more than two recesses. In some embodiments, the concave recess of the syringe engagement feature 22 is continuous about the circumference of the syringe barrel 12.

The syringe engagement feature 22, including its incorporated concave recesses 23, radially projects outwardly from the outer circumferential surface of the syringe barrel 12; it defines a circumferential, sloped ramp surface 25, which adjoins a tapered, non-luer tip 26. The non-luer tip 26 is at the distal end 14 of the syringe barrel 12. The syringe engagement feature 22 is located between the open proximal end 16 and the distal end 14 of the syringe barrel, adjoining the non-luer tip 26. The non-luer tip 26 is dimensioned such that it is not connectable to an intravenous device. The non-luer tip 26 defines a fluid pathway 29 in fluid communication with the chamber 20. In some embodiments, the syringe engagement feature 22 does not project outwardly from the outer circumferential surface of the syringe barrel. An anti-rotation key 28 projects from the syringe barrel 12. Some embodiments of the syringe do not have an anti-rotation key.

Figure 3:
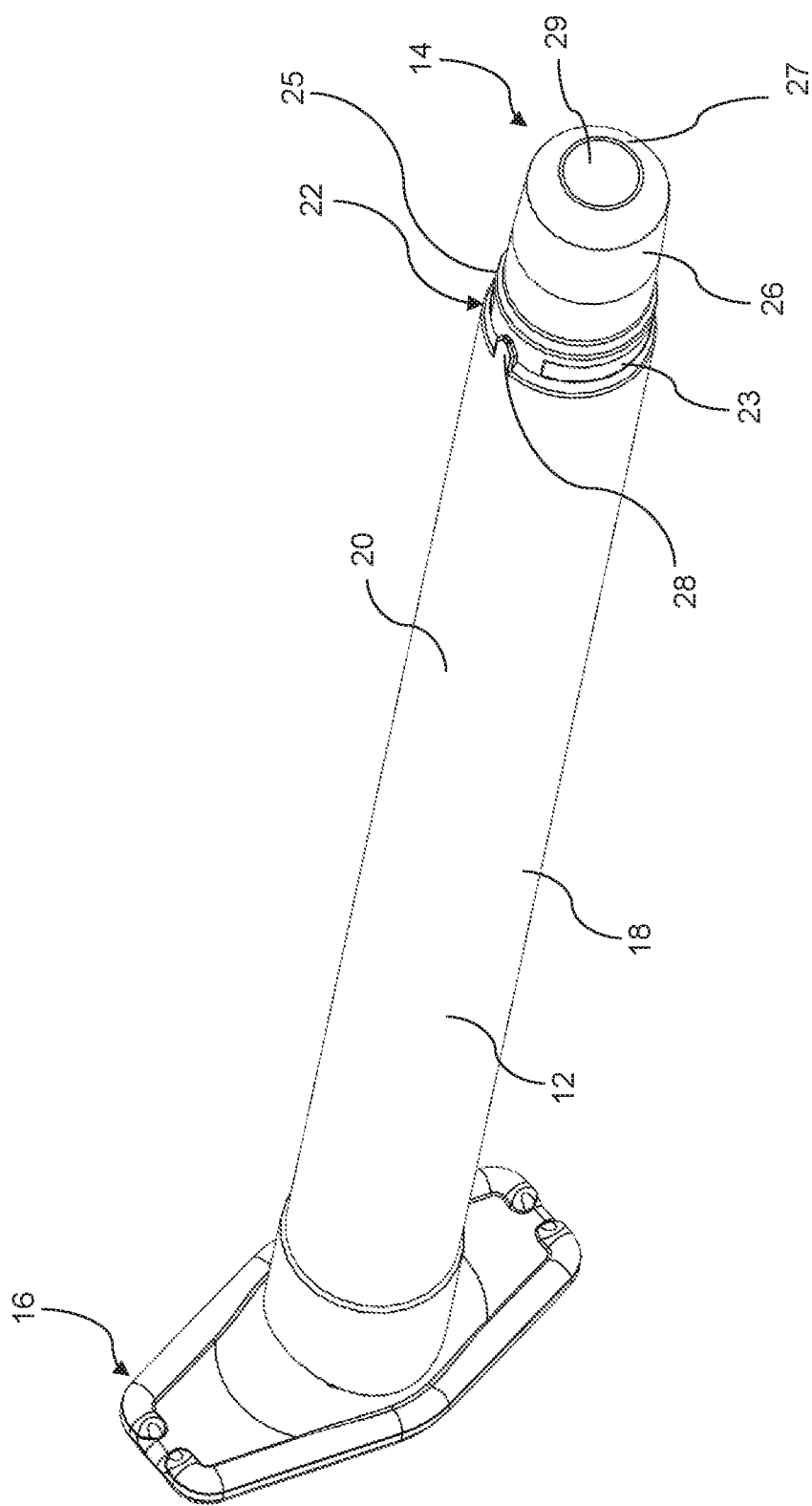
FIG. 3 is a perspective view of the syringe shown in FIG. 1.
Figure 5:
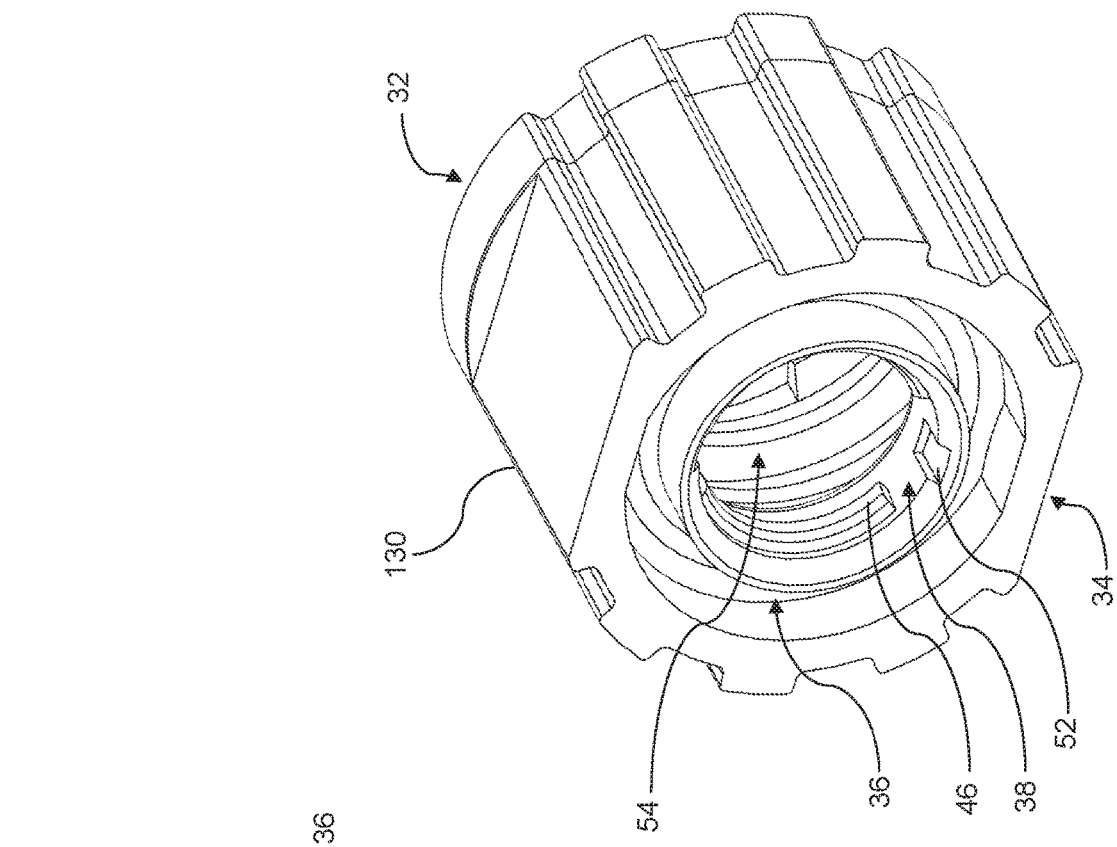
FIG. 5 is a perspective view of a collar according to another embodiment.
Figure 4:
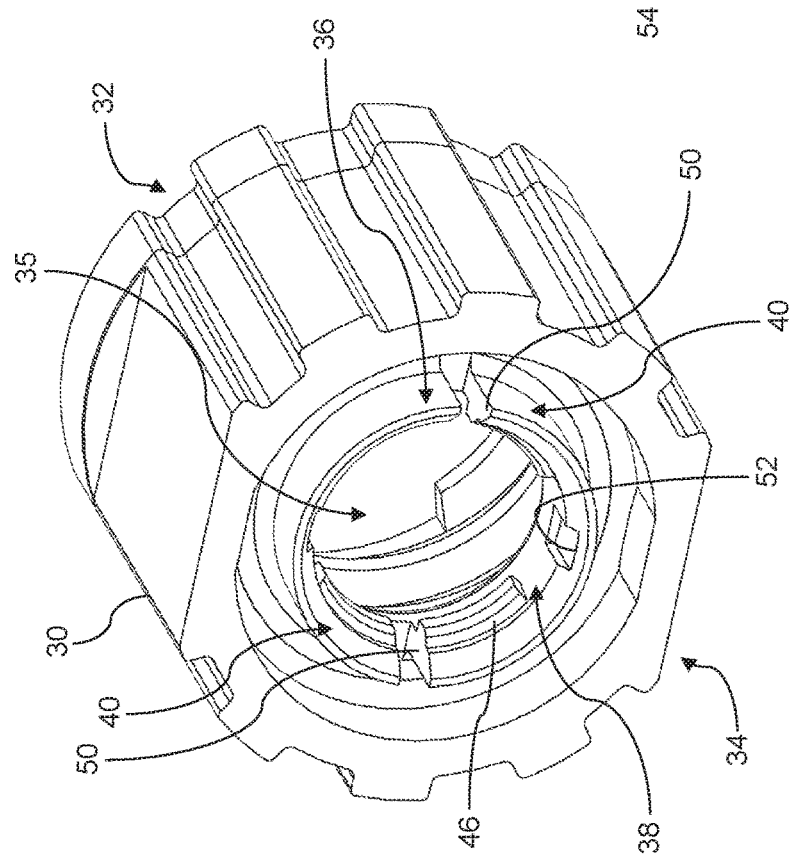
FIG. 4 is a perspective view of the collar of FIG. 1.

Referring to FIGS. 3-5, the syringe 10 further comprises an enteral collar 30 (collar) having a distal end 32 and a proximal end 34. A through-bore 35 (bore) defined within an inner surface of the collar 30 is in communication with the distal end 32 and the proximal end 34 of the collar 30. The proximal end 34 of the enteral collar 30 has a snap-in, enteral collar engagement feature 36 complementary to and engageable with the snap-in syringe engagement feature 22.

Figure 6:
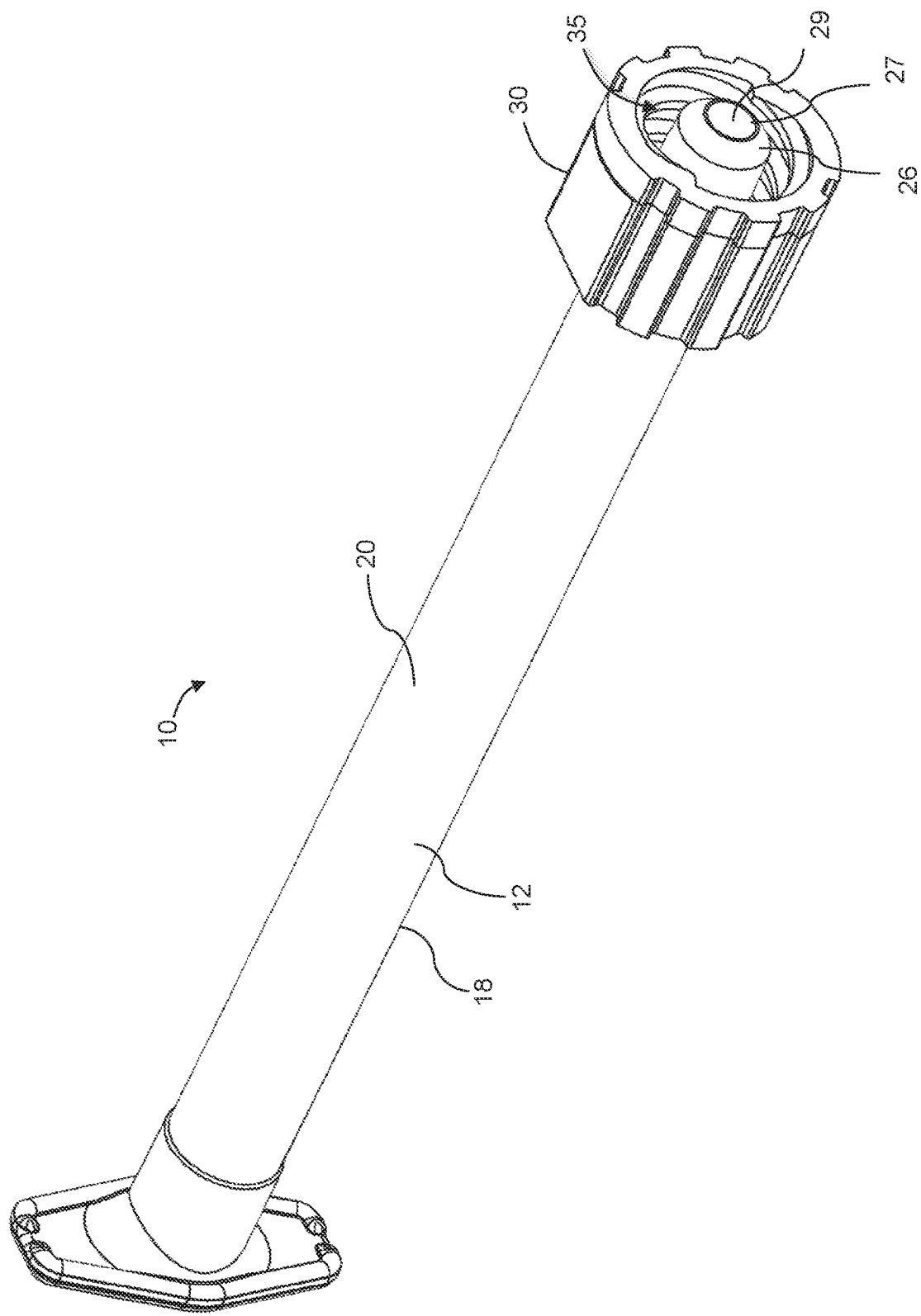
FIG. 6 is a perspective view of the syringe and collar shown in FIG. 1 mated with each other.
Figure 7:
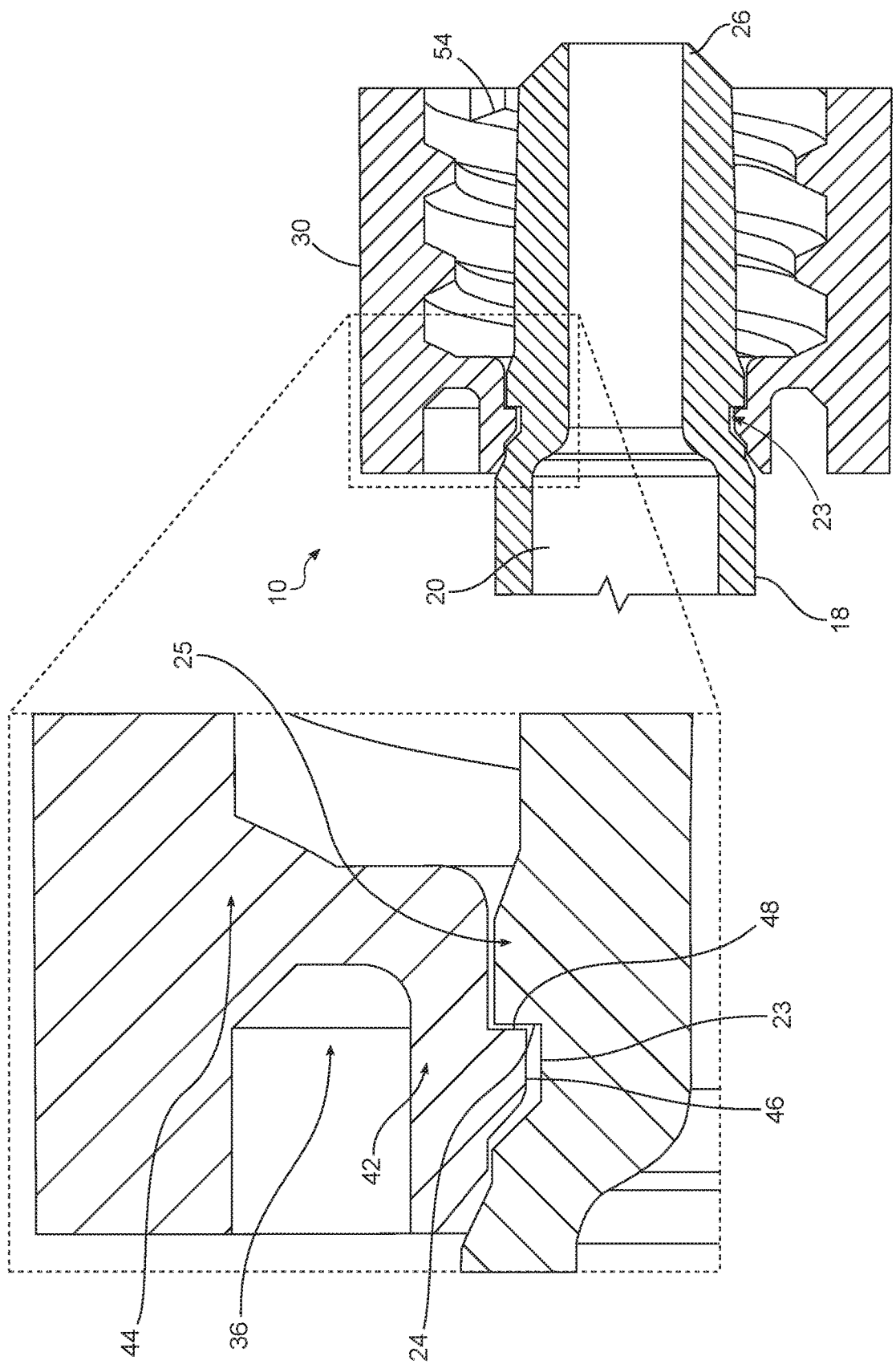
FIG. 7 is a planar axial cross-sectional view of the mated syringe and collar of FIG. 1.

As shown in FIGS. 6 and 7, the enteral collar 30 surrounds the non-luer tip 26 when the syringe engagement feature 22 is engaged with the enteral collar engagement feature 36. The enteral collar 30 is outside the fluid pathway 29 and not in fluid communication with the chamber 20. Fluid contained in the chamber 20 of the syringe 10 flows through distal tip 27; fluid flowing through the distal tip 27 is not in contact with the collar 30. Axial length of the non-luer tip 26 is greater than the axial length of the bore 35 of the enteral collar 30, so that the non-luer tip projects out of the distal end 32 of the enteral collar after engagement of the respective syringe engagement features 22 and enteral collar 36 engagement features. The enteral collar 30 is sized to permit connection to an enteral device and prevent connection to a device having a luer connector.

The enteral collar engagement feature 36 and the syringe engagement feature 22 include complementary snap-in/snap-fit mating features selected from cantilever snap joints, torsion snap-joints and annular snap-joints. Generally, the respective enteral collar engagement 36 and syringe engagement features 22 in the form of snap-in/snap-fit features comprise a concave recess formed on one of the engagement features and a complementary mating convex projection on the other of the engagement features. Referring to the embodiments shown in FIGS. 4-7, each respective concave recess 23 of the syringe engagement feature 22 mates with a convex hook or other protuberance formed in a corresponding enteral collar engagement feature 36.

In the embodiments of FIGS. 4-7, the enteral collar engagement feature 36 is a discontinuous annular snap joint 38, which includes at least one opposed pair of cantilever snap joints 40. Each of the snap joints 40 includes a cantilever arm 42, with a proximal end 44 of the arm coupled to a surface of the collar bore 35 of the enteral collar 30 and a hook 46 coupled to a distal end of the arm. Each hook 46 projects toward the centerline of the bore 35, for snap-in engagement with its corresponding concave recess 23 of the syringe engagement feature 22. Such snap-in engagement is accomplished by inserting and advancing the non-luer tip 26 of the syringe barrel 12 into the proximal side of the bore 35. As the syringe barrel 12 advances into the bore 35 each sloped ramp surface 25 the syringe engagement feature 22 abuts the tip of its corresponding hook 46, which deflects and biases its cantilever arm 42 in a direction away from the centerline of the bore. As each respective hook 46 axially clears its corresponding opposing sloped ramp surface 25 the cantilever arm 42 self-biases and snaps into its corresponding recess 23 of the syringe engagement feature 22 (shown in FIG. 7), accomplishing snap-fit/snap-in engagement of the mating enteral collar engagement feature 36 and its associated syringe engagement feature 22. Upon snap-in engagement of the respective syringe and enteral collar engagement features 22 and 36, the undercut surface 24 abuts against a corresponding axial surface 48 of the hook 46. In other embodiments, the orientation of the respective recess and the convex protuberance or hook are reversed, such that the cantilever arm 42 incorporates a recess or aperture, while the syringe engagement feature incorporates a mating hook that projects radially outwardly relative to the centerline of the bore 35. Thus, in some embodiments, the syringe engagement feature comprises a recess formed in the outer circumferential surface of the barrel, which captures an opposed projecting hook formed in the cantilever arm of the cantilever snap joint While a discontinuous annular snap joint 38 is shown in the embodiments of FIGS. 4 and 5, other embodiments incorporate a single cantilever snap joint or more than two cantilever snap joints. In some embodiments that incorporate a plurality of snap joints, they are oriented circumferentially about the bore 35 of the enteral collar 30: symmetrically or asymmetrically. The enteral collar 130 of FIG. 5 has a pair of opposed cantilever arms 42. The enteral collar 30 embodiment of FIG. 4 incorporates radially oriented relief cuts 50 in its proximal end 34, between cantilever arms 42 of the discontinuous annular snap joint 38. Thus, the collar 30 effectively comprises four cantilever arms 42: a pair, split by a relief cut 50 on one circumferential side and another pair, split by a relief cut 50 oriented 180 degrees on the other side. The relief cuts 50 facilitate easier radial deflection of the enteral collar 30 and deflection of its cantilever arms 42, as compared to the enteral collar 130 embodiment of FIG. 5, which does not have relief cuts. In some embodiments, the enhanced radial deflection of the enteral collar 30 and cantilever arm 42 flexure enabled by the relief cuts 50 facilitates easier insertion and advancement of a syringe barrel 12 into the collar. In other embodiments, the enhanced radial deflection and cantilever arm 42 flexure enabled by the relief cuts 50 enhances ability to separate the syringe barrel 12 and the enteral collar 30. Conversely, in the embodiment of FIG. 7, after engagement of the syringe engagement feature 22 and the enteral collar engagement feature 36, the enteral collar 30 is not removable from the syringe 10; the abutting surfaces of the undercut surface 24 and the corresponding axial surface 48 of the hook 46 inhibit disengagement of each respective cantilever arms 42 from its corresponding recess 23. In different exemplary embodiments, the overall force needed to advance and engage the syringe barrel 12 and collar 30 or the collar 130 relative to each other is selectively varied during syringe design by varying one or more of the cantilever arm 42 axial length and/or cross section, dimensions of fillet radius of the cantilever arm proximal end 44 attachment to the bore 35, and relative engagement surface area of the axial surface 48 of the hook 46 to the undercut surface 24 of the recess 23. In some embodiments, a shift of the hook 46 relative to the concave recesses 23 can vary the hook engagement during insertion and advancement of the collar.

Each of the enteral collar embodiments 30 and 130 of FIGS. 4 and 5 incorporates a keyway 52 on its respective proximal end 34, which mates with the anti-rotation key 28 of the syringe barrel 12 (shown in FIG. 3), after insertion of the syringe barrel into the collar and mating engagement of the syringe engagement feature 22 and the enteral collar engagement feature 36. After such engagement, the enteral collar 30 or 130 is not rotatable with respect to the syringe 10. In other embodiments, the anti-rotation feature is accomplished by forming corresponding, mating male and female asymmetric cross-sectional profiles on the outer circumference the syringe barrel 12 and in the bore 35 of the enteral collar embodiments 30 or 130.

As shown in FIGS. 1, 4, and 7, the surface of the enteral collar 30 defining the bore 35 comprises female collar threads 54 at the distal end 32 of the collar, for engaging a male threaded, non-luer connector (not shown). The threads 54 are axially spaced from the enteral collar engagement feature 36 that is oriented on the proximal end 34 of the collar 30. In other embodiments, the enteral collar 30 incorporates external male threads or a lug, rather than internal female threads with syringe threads (not shown) adjacent the distal end 14 of the syringe barrel 12. In other embodiments, the enteral collar 30 incorporates a manifold structure (not shown) on its distal end 32 with a plurality of male and/or female threaded surfaces, for coupling to a plurality non-luer connectors. In specific embodiments, the enteral collar 30 having the male thread or lug provides a male connector that provides an ENfit connection that conforms to ISO 80369-3 and is connectable with a female ENfit connector that conforms to ISO 80369-3.

Syringes usually retain some volume of medication in spaces within the chamber between the plunger and the distal end of the chamber, and these spaces are typically referred to as the "dead space" of the syringe. In one or more embodiments, when the chamber 20 of the syringe 10 has a volume of less than 5 ml, and a dead space region that retains fluid in the chamber after fluid is expelled from the chamber, wherein the dead space region contains less than 0.07 ml of fluid. In one or more embodiments, a syringe 10 with a chamber 20 having a volume in a range of 5 ml and less than 10 ml has a dead space region less than or equal to 0.075 ml. In one or more embodiments, a syringe 10 with a chamber 20 having a volume of less than 20 ml and greater than 10 ml has a dead space region less than or equal to 0.10 ml.

In one or more embodiments, the syringes described in this disclosure may be connected to a variety of known enteral devices, for example, feeding bags and feeding catheters, which is typically accomplished by connecting the enteral collars described herein to flexible tubing. The components of the syringes 10, including the syringe barrel 12 and the enteral collars 30, 130 are be fabricated of a variety of materials suitable for medical and health care applications. For example, the female or male adapters may be fabricated from a medical-grade material, such as, but not limited to, nylon, polypropylene, polycarbonate, polyvinylidene fluoride, acrylonitrile butadiene styrene, and polyvinyl chloride.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe comprising:
    a syringe barrel having a distal end, an open proximal end, and a sidewall extending between the distal end to the open proximal end, the sidewall defining a chamber, an outer circumferential surface, and a snap-in, syringe engagement feature oriented on the outer circumferential surface adjacent the distal end thereof;
    a non-luer tip oriented on the distal end of the syringe barrel, dimensioned such that the non-luer tip is not connectable to an intravenous device, the non-luer tip defining a fluid pathway in fluid communication with the chamber;
    an enteral collar, defining a bore in communication with a distal end and a proximal end thereof, the bore having a snap-in, enteral collar engagement feature oriented at the proximal end of the enteral collar that is complementary to and engageable with the syringe engagement feature, the enteral collar engagement feature selectively biased initially in a direction away from a centerline of the bore upon initial axial insertion and advancement of the tip of the syringe into the bore and then biased in a direction toward the bore centerline upon snap-in engagement with the syringe engagement feature, wherein the respective enteral collar engagement and syringe engagement features comprise a concave recess formed in the outer circumferential surface of the barrel and a complementary mating convex projection comprising a cantilever arm coupled to the bore of the enteral collar, and wherein the concave recess captures an opposed projecting hook formed on the cantilever arm; and
    the enteral collar surrounding the non-luer tip when the syringe engagement feature is engaged with the enteral collar engagement feature, and the enteral collar being sized to permit connection to an enteral device and prevent connection to a device having a luer connector.

2. The syringe of claim 1, wherein the enteral collar engagement feature comprises at least one cantilever snap joint.

3. The syringe of claim 2, further comprising a plurality of cantilever snap joints oriented circumferentially about the bore of the enteral collar.

4. The syringe of claim 3, the enteral collar further comprising a relief cut formed in the proximal end thereof between a pair of cantilever snap joints.

5. The syringe of claim 1, wherein the proximal end of the enteral collar includes the syringe engagement feature and the distal end of the enteral collar includes threads formed in the bore thereof, for engaging a threaded, non-luer connector.

6. The syringe of claim 5, wherein all the threads are axially separated from the enteral collar engagement feature.

7. The syringe of claim 1, wherein after mating engagement of the syringe engagement feature and the enteral collar engagement feature, the enteral collar is not separable from the syringe.

8. The syringe of claim 1, further comprising mating anti-rotation features formed respectively in the outer circumferential surface of the syringe barrel and in the bore of the enteral collar, so that the enteral collar is not rotatable with respect to the syringe after mating engagement of the syringe engagement feature and the enteral collar engagement feature.

9. The syringe of claim 1, wherein the chamber has a volume in a range of 5 ml and less than 10 ml, and a dead space region that retains fluid in the chamber after fluid is expelled from the chamber, wherein the dead space region contains less than 0.075 ml of fluid.

10. The syringe of claim 1, wherein axial length of the non-luer tip is greater than the axial length of the bore of the enteral collar, so that the non-luer tip projects out of the distal end of the enteral collar after engagement of the respective syringe and enteral collar engagement features.

11. The syringe of claim 1, wherein the enteral collar is outside the fluid pathway and not in fluid communication with the chamber.

12. The syringe of claim 1, further comprising radially oriented relief cuts formed in the proximal end of the enteral collar.

13. A syringe comprising:
    a syringe barrel having a distal end, an open proximal end, and a sidewall extending between the distal end to the open proximal end; the sidewall defining a chamber, an outer circumferential surface and a snap-in, syringe engagement feature radially projecting from the outer circumferential surface adjacent the distal end thereof;
    a non-luer tip oriented on the distal end of the syringe barrel, dimensioned such that the non-luer tip is not connectable to an intravenous device, the non-luer tip defining a fluid pathway in fluid communication with the chamber;

an enteral collar, defining a bore having a centerline in communication with a distal end and a proximal end thereof, threads formed in the bore on the distal end thereof, for engaging a threaded, non-luer connector, the bore having a snap-in, enteral collar engagement feature oriented at the proximal end of the enteral collar that is complementary to and engageable with the syringe engagement feature, the enteral collar engagement feature axially separated from the threads;

a concave recess formed on one of the engagement features and a complementary mating convex projection on the other of the engagement features, the complementary mating convex projection comprising at least one cantilever snap joint including a cantilever arm, a proximal end of the cantilever arm coupled to the bore of the enteral collar and a hook coupled to the distal end of the arm, the hook projecting toward the centerline of the bore for snap-in engagement with the concave recess;

the enteral collar engagement feature selectively biased initially in a direction away from a centerline of the bore upon initial axial insertion and advancement of the tip of the syringe into the bore and then biased in a direction toward the bore centerline upon snap-in engagement with the syringe engagement feature; and the enteral collar surrounding the non-luer tip when the syringe engagement feature is engaged with the enteral collar engagement feature, and the enteral collar being sized to permit connection to an enteral device and prevent connection to a device having a luer connector.

14. The syringe of claim 13, wherein the syringe engagement feature includes the concave recess.

15. The syringe of claim 14, further comprising a plurality of cantilever snap joints circumferentially about the bore of the enteral collar and a corresponding concave recess of the syringe engagement feature.

16. The syringe of claim 15, further comprising a relief cut formed in the proximal end of the enteral collar between a pair of cantilever snap joints.

17. The syringe of claim 15, wherein
the enteral collar engagement feature is formed as a discontinuous annular snap joint.

18. The syringe of claim 17, further comprising a relief cut formed in the proximal end of the enteral collar between a pair of the cantilever snap joints.

\* \* \* \* \*